(12) United States Patent
Gotzmann et al.

(10) Patent No.: US 7,345,168 B2
(45) Date of Patent: *Mar. 18, 2008

(54) PROCESS FOR THE PREPARATION OF POLYPHOSPHATES OF ORGANIC BASES

(75) Inventors: Karl Gotzmann, deceased, late of Budenheim (DE); by Liselotte Götzmann, legal representative, Budenheim (DE); Hans-Dieter Nagerl, Dudenhofen (DE); Thomas Futterer, Wieshaden (DE)

(73) Assignee: Chemische Fabrik Budenheim KG, Budenheim (DE)

( * ) Notice: Subject to any disclaimer, the term of this patent is extended or adjusted under 35 U.S.C. 154(b) by 381 days.

This patent is subject to a terminal disclaimer.

(21) Appl. No.: 10/489,369

(22) PCT Filed: Aug. 22, 2002

(86) PCT No.: PCT/DE02/03065

§ 371 (c)(1),
(2), (4) Date: Aug. 9, 2004

(87) PCT Pub. No.: WO03/024945

PCT Pub. Date: Mar. 27, 2003

(65) Prior Publication Data

US 2004/0260089 A1    Dec. 23, 2004

(30) Foreign Application Priority Data

Sep. 13, 2001 (DE) .................. 101 45 093

(51) Int. Cl.
*C07D 251/00* (2006.01)
(52) U.S. Cl. ............... 544/214; 544/358; 544/195
(58) Field of Classification Search ............... 544/214, 544/358, 195; 558/154
See application file for complete search history.

(56) References Cited

U.S. PATENT DOCUMENTS 6,114,421 A * 9/2000 Malcangi .................. 524/100

* cited by examiner

*Primary Examiner*—Rei-tsang Shiao
(74) *Attorney, Agent, or Firm*—Dinsmore & Shohl LLP

(57) ABSTRACT

A simple and economical process for the preparation of polyphosphates of organic bases consists of reacting a mixture of phosphorus pentoxide and at least one organic nitrogen base with at least one compound which releases water accompanied by decomposition under the prevailing conditions in such a molar ratio that upon decomposition of the water-releasing compound at most essentially 2 mol. water are produced per mol. phosphorus pentoxide. Thus-prepared polyphosphates are particularly suitable as flame-protection agents for plastics.

6 Claims, No Drawings

PROCESS FOR THE PREPARATION OF POLYPHOSPHATES OF ORGANIC BASES

This application is a 371/DE 02/03065 filed on Aug. 22, 2002.

Polyphosphates of organic nitrogen bases such as guanidine and melamine are becoming increasingly important as flame-protection agents in plastics and as a flame-retardant finish for textiles. Polyphosphate mixtures used as flame-protection agents for plastics are intended to decompose as close as possible to the decomposition point of the plastic, as too-low decomposition points already lead to decomposition and thus to the formation of steam and undesired blistering in the plastics product during the preparation of the mixture of plastic and flame-protection agent. To avoid such undesirably low decomposition points of the flame-protection agent, the polyphosphate mixtures should contain no orthophosphate if at all possible and where necessary also no pyrophosphate.

Various process types for the preparation of polyphosphates of organic bases are known to date, however these known processes all have specific disadvantages.

A process type for the preparation of polyphosphates of organic bases consists of firstly preparing an orthophosphate of the organic base and then converting same into polyphosphates of the organic base by heating to a temperature over 300° C. This process is described for example in WO 97/44 377. The required relatively high temperatures of this process type make the process uneconomical if it is considered in particular that flame-protection agents are mass-produced products. According to U.S. Pat. No. 6,114,421, specific organic nitrogen bases are reacted with phosphoric anhydride in specific concentrations and under specific reaction conditions.

Another process type consists of neutralizing polyphosphoric acid customary in the trade with the organic base. Polyphosphoric acids customary in the trade are however mixtures which contain ortho- and pyrophosphoric acid so that the product mixtures contain the undesired ortho- and pyrophosphate of the organic base. In addition, the polyphosphoric acids customary in the trade are viscous to solid and difficult to process. The ortho- and pyrophosphates contained are converted into polyphosphates only at temperatures above 306° C. which results in the same disadvantage as the first process type described above.

A third process type starts with alkaline polyphosphate or alkaline pyrophosphate which are dissolved in water and acidified with HCl. To remove the chloride ions, the products must be washed and dried, which makes the process time-consuming and laborious. When used as flame-protection agents, the flame-protection agent must not contain chloride ions as they can lead to harmful by-products.

The object of the invention was thus to create a simple and economical process for the preparation of polyphosphates of organic bases while avoiding the disadvantages of the state of the art, the products being intended to be as free as possible from orthophosphates and where necessary also from pyrophosphates.

The process according to the invention which achieves this object consists of reacting a mixture of phosphorus pentoxide and at least one organic nitrogen base with at least one compound which releases water accompanied by decomposition under the reaction conditions in such a molar ratio that during decomposition of the water-releasing compound at most essentially 2 mol. water are produced per mol. phosphorus pentoxide. Polyphosphates within the meaning of the invention are condensed phosphates with a chain length of at least 2.

Surprisingly the problem of the state of the art of distributing the required water quantity homogeneously and uniformly in the mixture of phosphorus pentoxide and base is thus solved. The required quantity of water is distributed completely homogeneously and uniformly in the customarily introduced mixture of phosphorus pentoxide and organic nitrogen base so that a local oversupply of water which leads to the formation of ortho- and pyrophosphoric acid is avoided.

Regardless of the preparation process, the object of the invention is achieved by a mixture of polyphosphates of organic nitrogen bases which have a) a weight loss upon heating to 320° C. of less than 2 wt.-%, b) a pH value of a 10-% aqueous suspension at 25° C. of >5, preferably of 5.2 to 7.7, particularly from 5.8 to 7.0; and c) a solubility in water at 25° C. of less than 0.1, preferably less than 0.01 g/100 ml water.

Such polyphosphate mixtures can be expediently prepared according to the process according to the invention described above.

There can be considered in principle as water-releasing compounds all those which decompose under the selected reaction conditions accompanied by the formation of water, such as for example substances containing crystallization water, borax, aluminium hydroxide or magnesium hydroxide, which however can be used only if the decomposition products of these compounds do not interfere with or are even advantageous in the polyphosphate mixtures when used. Preferably used as water-releasing compounds are those which, in addition to water, release only volatile decomposition products, preferably oxalic acid in anhydrous form or as dihyrdrate or formic acid which upon decomposition, in addition to water, produce only carbon dioxide and carbon monoxide which leave the reaction mixture on account of their volatility.

The molar ratios in the reaction mixture are to be set according to the above statements such that at most approx. 2 mol. water are produced per mol. $P_2O_5$ in the reaction mixture. It is to be taken into account that 1 mol. oxalic acid (anhydrous) produces 1 mol. water upon decomposition and oxalic acid dihydrate produces 3 mol. water. In the preparation of pyrophosphate, the starting substances are used in such a molar ratio that essentially 2 mol. water are produced per mol. $P_2O_5$ in the water-releasing compound. In the preparation of long-chained polyphosphates, this value is approx. 1 mol. water per mol. $P_2O_5$. When the term "approx." or "essentially" is used in this description, the value is usually ±10, preferably ±5% of the value given.

As organic nitrogen base there can be used for this purpose a per-se known nitrogen base such as for example polyvinylamine, polyethyleneimine, piperazine, methylenediamine, melamine, guanidine, methylolmelamine or their condensates and also their mixtures. Melamine and guanidine are preferred. Assuming that the nitrogen bases have a base radical, the molar ratio is to be set such that if pyrophosphate is obtained as desired and the pyrophosphate is completely saturated with base radicals, essentially 2 mol. base must be used per P atom in the product. If long-chained polyphosphates are intentionally obtained, the molar ratio of base:P used is to be essentially 1:1 (base: $P_2O_5$ essentially 2:1). By setting the molar ratio, the saturation with base radicals can be varied.

The reaction according to the invention can take place at ambient temperature, however it is too slow for practical purposes as a rule. It is therefore preferred to carry out the reaction at an increased temperature, in particular in the range from 100 to 250° C., preferably 180 to 250° C., particularly preferably 200 to 220° C. The preferred minimum temperature of 200° C. is above the melting temperature of oxalic acid, which has a positive effect on the reaction of the components. On the other hand, the temperatures to be applied are well below the temperatures of over 300° C. required with the known processes. This makes the process economical, bearing in mind that as a result of the homogeneous distribution of the water in the reaction mixture the formation of orthophosphate and where necessary pyrophosphate is avoided.

The procedure for the process according to the invention is preferably that the required quantity of phosphorus pentoxide is mixed with the organic nitrogen base, the mixture is taken to the desired temperature and the required quantity of water-releasing compound is then added and homogeneously distributed in the reaction mixture by mixing.

The polyphosphate mixtures according to the invention are advantageously used as flame-protection agents for plastics, preferably thermoplasts, in particular polyamides and polyesters.

The following examples serve to further explain the invention.

EXAMPLE 1

An oil-heated double-Z kneader with an effective volume of 5 l is charged with 1250 g (10 mol.) melamine and 710 g (5 mol.) phosphorus pentoxide. The mixture is homogenized and heated to a temperature of 220° C.

Within 15 minutes 450 g (5 mol.) of anhydrous oxalic acid are then added and mixed in. After the addition, there is a secondary reaction time of 15 min before the melamine polyphosphate produced is removed from the kneader.

EXAMPLE 2

In the same kneader as described in Example 1, 1260 g (10 mol.) melamine and 710 g (5 mol.) phosphorus pentoxide are mixed and heated to 220° C. As in Example 1, however, 900 g (10 mol.) anhydrous oxalic acid are introduced within 15 min. After a further 15 min at 220° C., pure dimelamine pyrophosphate is removed from the kneader.

EXAMPLE 3

3780 g melamine (30 mol.) are mixed with 2130 g (15 mol.) phosphorus pentoxide in a laboratory ploughshare mixer with an effective volume of 10 l and thermal oil-heated double jacket and heated to a temperature of 200° C. Within 30 min, 630 g (5 mol.) oxalic dihydrate are then added. After a secondary reaction time of a further 15 min, the melamine polyphosphate formed was removed from the mixer.

EXAMPLE 4

In the same mixture as described in Example 3, 5400 g (30 mol.) guanidine carbonate are mixed with 2130 g (15 mol.) phosphorus pentoxide and heated to a temperature of 250° C. 1350 g (15 mol.) anhydrous oxalic acid are added in metered doses over a period of 1 h. After a further hour's secondary reaction time, the guanidine polyphosphate formed is removed from the mixer.

EXAMPLE 5

In a kneader according to Examples 1 and 2, 861 g (10 mol.) piperazine are mixed with 710 g (5 mol.) phosphorus pentoxide and heated to 100° C. Within 15 min, 210 g (1.7 mol.) oxalic dihydrate are then added. The secondary reaction time is 1 h before the piperazine polyphosphate formed is removed.

The invention claimed is:

1. A process for preparing polyphosphates of organic bases comprising reacting phosphorus pentoxide, at least one organic nitrogen base selected from the group consisting of piperazine, methylenediamine, melamine, guanidine, methylolmelamine or condensates and mixtures thereof, and at least one water releasing compound which releases water accompanied by decomposition under the reaction conditions in such a molar ratio that upon decomposition of the water-releasing compound, at most essentially 2 mol. water are produced per mol. phosphorus pentoxide.

2. A process as claimed in claim 1 in which said at least one water-releasing compound comprises a water of hydration-containing compound selected from the group consisting of borax, aluminum hydroxide, magnesium hydroxide, and mixtures thereof.

3. A process as claimed in claim 1 in which said reaction is carried out at a temperature of from about 100 to about 250° C.

4. A process as claimed in claim 1 in which said reaction is carried out at a temperature of from about 180 to about 250° C.

5. A process as claimed in claim 1 in which said reaction is carried out at a temperature of from about 200 to about 220° C.

6. A process as claimed in claim 1 in which said at least one water-releasing compound comprises oxalic acid anhydrate, oxalic acid dihydrate, or formic acid.

* * * * *